United States Patent [19]
Clewett et al.

[11] Patent Number: 5,334,204
[45] Date of Patent: Aug. 2, 1994

[54] FIXATION SCREW

[75] Inventors: Richard H. Clewett, Los Angeles; Claude O. Pering, Ranchos Palos Verdes; Daniel B. Sharitz, Lawndale, all of Calif.

[73] Assignee: Ace Medical Company, Los Angeles, Calif.

[21] Appl. No.: 924,315

[22] Filed: Aug. 3, 1992

[51] Int. Cl.⁵ ............................................. A61B 17/56
[52] U.S. Cl. ....................................... 606/73; 606/79
[58] Field of Search ..................... 606/72, 73, 65, 66, 606/67, 79; 441/387, 178, 395, 386

[56] References Cited

U.S. PATENT DOCUMENTS

| | | | |
|---|---|---|---|
| 2,414,882 | 1/1947 | Longfellow | 128/92 |
| 3,744,488 | 7/1973 | Cox | 128/92 |
| 4,059,102 | 11/1977 | Devas | 128/92 |
| 4,295,351 | 10/1981 | Bjorklund et al. | 72/38 |
| 4,463,753 | 8/1984 | Gustilo | 128/92 |
| 4,468,200 | 8/1984 | Münch | 433/174 |
| 4,537,185 | 8/1985 | Stednitz | 128/92 |
| 4,569,338 | 2/1986 | Edwards | 128/69 |
| 4,640,271 | 2/1987 | Lower | 128/92 |
| 4,653,486 | 3/1987 | Coker | 128/92 |
| 4,940,467 | 7/1990 | Tronzo | 606/66 |
| 4,950,270 | 8/1990 | Bowman et al. | 606/72 |
| 4,978,350 | 12/1990 | Wagenknecht | 606/72 |
| 5,019,079 | 5/1991 | Ross | 606/73 |
| 5,047,030 | 9/1991 | Draenert | 606/65 |
| 5,098,435 | 3/1992 | Stednitz et al. | 606/73 |
| 5,120,171 | 6/1992 | Lasner | 411/308 |
| 5,129,901 | 7/1992 | DeCoste | 606/65 |

OTHER PUBLICATIONS

Smith & Nephew Richards, *1992 Orthopaedic Catalog*, pp. H2 and H5.
Zimmer Inc., *MAGNA-Fx Cannulated Screw Fixation System Catlog*. Aug. 1989.
Howmedica, *1991 Product Catalog*, p. H8.
Synthes (U.S.A.), *The Large Cannulated Screw System*, 1989.
Synthes (U.S.A.), *1987 Catalog with 1990 Supplement*, pp. 2–595, 1990.
1 sheet illustrating screws from Synthes, Howmedica, Zimmer and Richards.

Primary Examiner—Robert A. Hafer
Assistant Examiner—David J. Kenealy
Attorney, Agent, or Firm—Kinney & Lange

[57] ABSTRACT

A fixation screw for attaching to a bone has at least one flute which traverses the proximal portion of the thread to form reverse cutting faces on the thread at the proximal portion. The cutting faces are arranged to cut the bone when the screw is rotated in a reverse rotational direction to ease in withdrawal of the screw. The flute forms a first plane containing the cutting faces on the thread and the axis of rotation of the screw. A base surface is formed by the flute forwardly of the cutting faces when the screw is rotated in a reverse direction. The base surface includes a rotational portion at the root diameter of the thread and a planar portion in a plane tangential to the rotational portion and arranged so that a substantial portion of the cutting face is axially offset from the leading thread to thereby engage the bone. Additionally or optionally, the thread is tapered at the proximal end to form a reverse self-tapping thread.

21 Claims, 2 Drawing Sheets

U.S. Patent  Aug. 2, 1994  Sheet 1 of 2  5,334,204
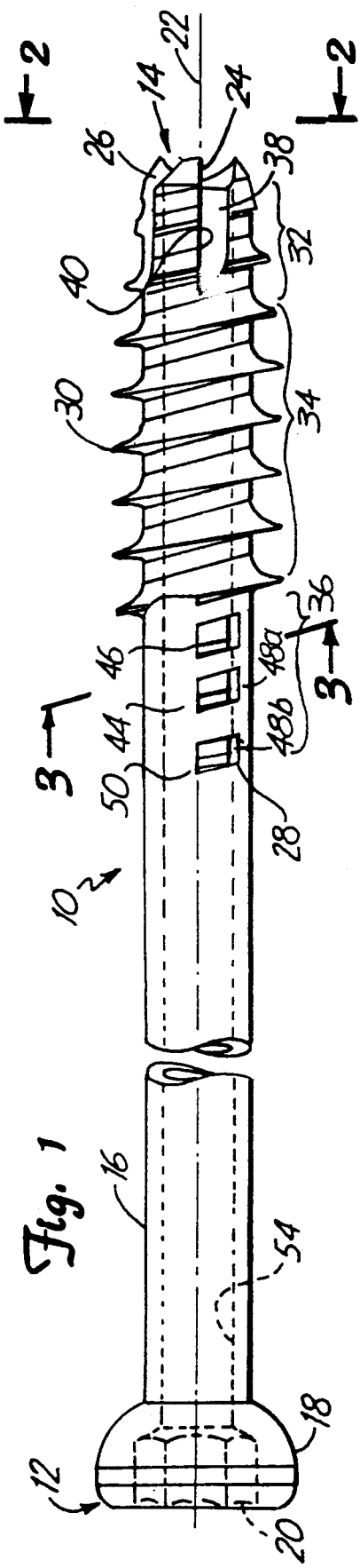
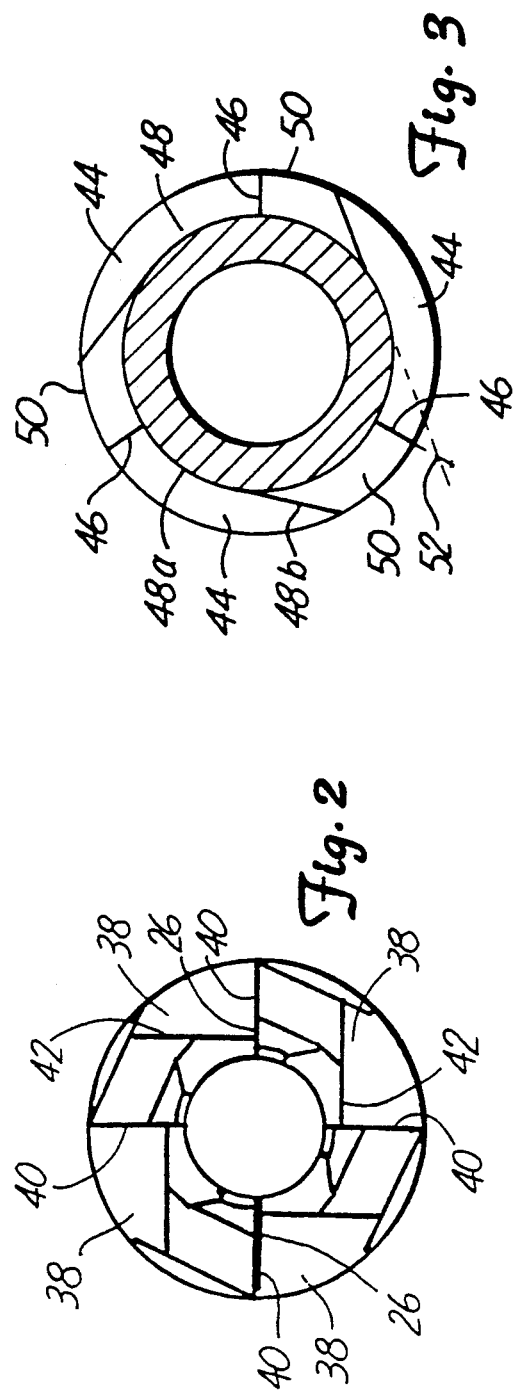

FIXATION SCREW

RELATED PATENTS

The following patent is related to the present invention and the disclosure of which is hereby incorporated by reference:

Denis P. Stednitz, U.S. Pat. No. 4,537,185 granted Aug. 27, 1985 for "Cannulated Fixation Screw".

BACKGROUND OF THE INVENTION

This invention relates to fixation screws for use in orthopedic applications.

It is well known that fractured bones may be effectively healed by fixing the fractured bone in a sufficiently secure position to prevent slippage or separation. With a bone so secured, bone tissue will grow and bone cells will multiply in the region of the fracture. One common technique for securing fractures is an external fixation pin or screw which extends into or through the bone fragments to secure the fragments in a fixed position. Typically, the fixation pin pierces the outer cortex of the fractured bone, crosses the medullary canal and embeds in the opposite cortex.

Early fixation pins were smooth, cylindrical shafts which were passed through predrilled holes. These pins had no thread to engage the bone fragments. Instead, the pin merely minimized slippage or separation. More recently, fixation screws have been employed to threadably engage the bone fragments to more securely fix the fragments in position. Fixation screws have been developed which include drilling faces and self-tapping threads with tapered and/or cutting threads.

The drilling feature of a fixation screw is accomplished through use of a wedge-shaped spade surface with knife edges which scrape away the bone upon rotation of the shaft. Self-tapping is accomplished by tapering the distal end of the thread at the drill point. Cutting threads are formed with flutes forming cutting faces at each convolution of thread, particularly in the tapered, self-tapping section.

The fixation screw often included a cannula through the shaft to permit a guide pin, mounted in a guide hole in the bone, to facilitate accurate positioning of the fixation screw. Cannulated self-drilling, self-tapping fixation screws represented a significant advance to orthopedic fixation techniques. A more thorough discussion of such devices may be found in the Stednitz U.S. Pat. No. 4,537,185, assigned to the same assignee as the present invention. One of the features of prior fixation screws resides in the fact that excess heat was not built up which could kill bone tissue. Moreover, many such pins were constructed of titanium which is sufficiently porous at its exterior surface as to permit bone growth to extend into the surface, thereby providing a more effective stabilization and healing of the bone. While these features enhanced and promoted the healing process, it sometimes occurred that the bone tissue would so thoroughly conform to the fixation screw as to make it difficult to remove the screw after the bone has healed.

Previously, fixation screws were removed or withdrawn from the fixing position by rotating the screw in a direction opposite to its insertion direction so that the thread reacts against the threaded channel in the bone to withdraw from the bone. However, if the bone has grown over the thread or into the porous surface of the screw (in the case of titanium screws), reliance on the pin shaft and existing threads to clear an opening for retraction of the screw has not always been possible. Moreover, the threaded portion of a fixation screw is usually only at the distal end of the screw which is embedded in the hard cortex on only the far side of the bone. The smooth shank extends through the outer cortex of the near side of the bone. The shank diameter is typically equal to or smaller than the root diameter of the thread, so that outer cortex bone growth in the near side of the bone conforming to the smooth surface of the shank is not easily penetrated by the withdrawing thread. More particularly, during withdrawal, the proximal end of the thread engages the cortex in the medullary canal. Since the cortex material is quite hard, the withdrawing screw often cannot easily penetrate the near cortex. Application of a greater withdrawing force can result in a free rotation of the screw in the medullary canal without entering the near cortex. If this occurs, an extractor tool must be attached to the screw to aid in its withdrawal.

Attempts have been made to employ a reverse self-tapping thread at the proximal end of the threaded portion of the bone screw to aid in the entering of the near cortex. The reverse self-tapping thread have heretofore met limited success. More particularly, prior self-tapping threads employed reverse flutes to form reverse cutting faces to cut into the bone during withdrawal of the screw. The flutes were formed by a 90° cut into the thread transversing several convolutions at the proximal end of the thread, the cut forming cutting faces with a base surface tangential to the minor, or root, diameter of the thread at the base of the cutting faces. However, the geometry of the flutes was such that the bone material was often first engaged by the thread portions forwardly (during reverse rotation to withdraw the screw) of the base surfaces of the flutes. Consequently, only a small portion of the reverse cutting faces formed by the flutes engaged the bone material, and the cutting faces were of minimal effectiveness. Moreover, the flutes forming prior reverse cutting threads formed a volume adjacent the screw surface which was too small to adequately collect bone chips created during the reverse cutting process. Also, it has not been possible to provide an effective taper to reverse self-tapping threads.

SUMMARY OF THE INVENTION

In one form of the invention, a fixation screw for attaching to a bone has at least one flute which traverses the proximal portion of the thread to form cutting faces on the thread at the proximal portion. The cutting faces are arranged to cut the bone when the screw is rotated in a reverse rotational direction. Preferably, the cutting faces on the thread are in a first plane formed by the flute and contain the axis of rotation of the screw. A base surface is formed by the flute forwardly of the cutting faces when the screw is rotated in a reverse direction. The base surface includes a rotational portion coincident with the root diameter of the thread and adjacent the cutting faces, and a planar portion forwardly of the rotational portion and in a plane tangential to the root diameter. The plane of the planar portion of the base intersects the first plane containing the cutting faces at an obtuse angle.

In another form of the invention, the crest diameter is tapered at the proximal end of the thread to provide a reverse self-tapping thread which is fully formed with sharp crests.

BRIEF DESCRIPTION OF THE DRAWINGS

FIG. 1 is a plan view of a fixation screw according to the presently preferred embodiment of the present invention.

FIG. 2 is a view of the distal end of the screw shown in FIG. 1 showing drilling means.

FIG. 3 is a section view taken at line 3—3 of FIG. 1 showing the proximal cutting thread in accordance with the present invention.

DETAILED DESCRIPTION OF THE PREFERRED EMBODIMENTS

Figure 4:
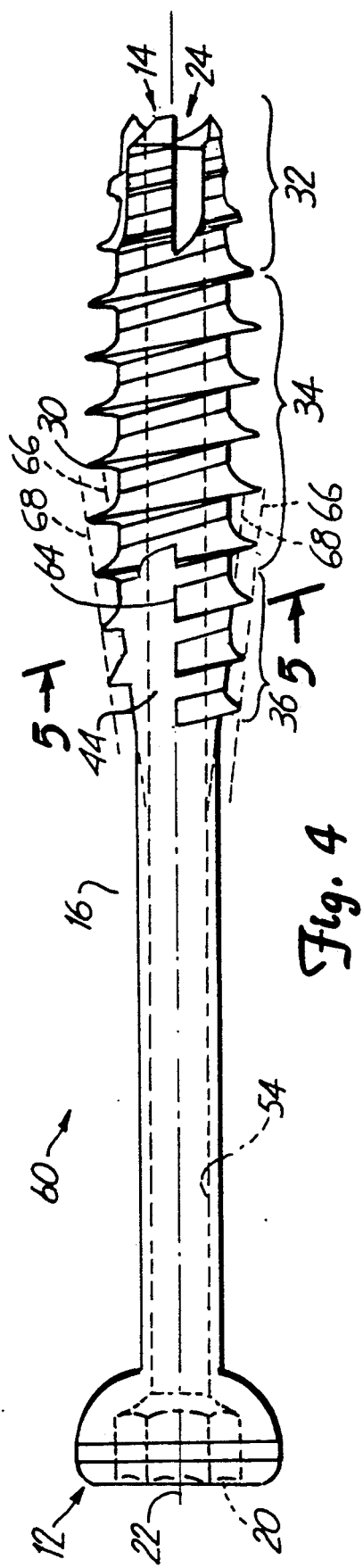
FIG. 4 is a plan view of a fixation screw in accordance with a modification of the present invention.

FIGS. 1-3 illustrate a fixation screw 10 in accordance with the presently preferred embodiment of the present invention. Screw 10 has a proximal end 12 and a distal end 14 with a shank 16 of selected diameter therebetween. Head 18 at the proximal end includes a generally hexagonally-shaped recess 20 arranged to accommodate an ordinary hexagonal drive wrench (not shown) to promote rotation of screw 10 about its axis 22. Distal end 14 includes a drilling tip 24 comprising a plurality of drilling teeth 26 arranged to drill a passage into a bone so that fixation screw 10 may enter the bone.

A plurality of convolutions of thread 30 are disposed along the shaft of screw 10 between the distal end 14 and a point 28 approximately midpoint between the distal and proximal ends. The convolutions of thread 30 are of equal pitch and are arranged in three successive and adjacent groups 32, 34 and 36. The thread of groups 34 and 36 of convolutions is configured with a root diameter equal to the diameter of the shank 16 and a fixed, design crest diameter. The thread of group 32 of convolutions is configured with crest and root diameters which are tapered between a large diameter at the intersection between groups 32 and 34 to a small diameter at distal end 14. Thus, the crest and root diameters of group 32 of convolutions are smaller than the crest and root diameters of groups 34 and 36. At least one, and preferably a plurality (up to four), flutes 38 transverse the convolutions of thread of group 32 to form cutting faces 40. A base surface 42 orthogonal to cutting faces 40 are formed by flutes 38, the base surfaces and cutting faces being arranged so that flutes form an opening to permit the cutting faces to engage the bone to cut the bone upon rotation of screw 10 about its axis 22 in a first, forward rotational direction.

The thread of group 36 of convolutions proximal to and adjacent group 34 is a reverse cutting thread. More particularly, at least one, and optionally a plurality (up to three), flutes 44 transverse the convolutions of thread in region 36. Flutes 44 are formed by cutting into the thread to at least the surface of the minimal root diameter (which is the same diameter as the shank of the screw) to form cutting faces 46 extending radially from the shaft. A surface 48 is formed at the base of the flute. Surface 48 includes at least a rotational portion 48a at the radius of the root, or shank, diameter and a planar portion 48b extending tangentially to the root, or shank, diameter to the crest diameter. Flutes 44 define a plurality of lands 50 between them with each of the lands including a portion of thread 30.

As shown particularly in FIG. 3, there may be a plurality of flutes 44 defining cutting faces 46, although presently only one flute is preferred. The nominal planes of faces 46 and surface 48b intersect to form a projected obtuse angle between the cutting faces and surface 48b. Preferably, the intersection is at a line (shown as point 52 in FIG. 3) parallel to axis 22 at least as distant from the axis, and preferably beyond, as the crest diameter.

Preferably, the fixation screw includes a cannula 54 for purposes described in U.S. Pat. No. 4,537,185.

FIG. 4 shows a fixation screw 60 in accordance with a modification of the present invention. Screw 60 includes a proximal end 12 and distal end 14, the proximal end having a head 18 and receptacle 20 as in the case of screw 10 shown in FIGS. 1-3. Distal end 14 has a drilling means 24, as previously described, and the screw has a plurality of convolutions of thread 30 with distal group 32 and intermediate group 34 essentially as previously described. The convolutions of thread in group 36 include flutes 44 forming cutting faces 46 as heretofore described.

As shown in FIG. 4, the root diameter 62 of the thread in portion 34 is greater than the diameter of shank 64. Hence, the screw shown in FIG. 4 is most advantageous for screws with thread diameters larger than the screw shown in FIGS. 1-3. In the case of FIG. 4, the crest and root diameters of the thread in portion 36 are tapered at the same or similar angles to the axis of the screw to form a tapered thread whose root and crest diameters diminish in size from the root and crest diameters of the thread in portion 34 to the shank diameter. Hence, the tapered thread of portion 36 provides a sharp crest at the same pitch as the other thread portions with tapering of the root and crest diameters along nominal planes 66 and 68. Unlike prior cut tapers which result in flat crests, the tapering of both the root and crest diameters permits a sharp crest to penetrate the bone material and aid in the withdrawal of the screw.

In the use of the fixation screw in accordance with the present invention, a hex driver is assembled to hex receiver 20 and the drilling end 24 of the fixation screw is applied to the bone. Typically, a locating pin or other guide is applied through cannula 54 to aid in accurate placement of the fixation screw as described in the aforementioned Stednitz patent. The screw is rotated clockwise (to the surgeon) so that the drill teeth bite into the bone to clear a passageway for the screw. The cutting faces 40 formed by flutes 38 cut into the cortex material of the bone to form a threaded path for the thread 30 on screw 10. The tapered thread in group 32 of convolutions tap into the bone to aid in inserting the screw into the bone. The screws continue to thread into the outer cortex on the entrance, or near, side of the bone, and thereafter through the softer medullary canal and into the outer cortex on the opposite, or far, side of the bone. Continued rotation and pressure applied to the screw forces the screw into the outer cortex on the opposite side of the bone to fix the position of the fractured bone to that desired by the surgeon. In a typical procedure, the fixation screw remains threaded into the outer cortex on the opposite, or far, side of the bone with midpoint 28 (where the proximal end of the thread 30 meets shank 16) usually being located in the medullary canal. As a result, only shank 16 extends through the originally tapped outer cortex on the entrance, or near, side of the bone. The guide pin and other paraphernalia are removed in the usual fashion, leaving the fixation screw securely fixing the position of the fractured bone for the healing process.

When it is necessary to remove screw 10 from the bone, it often occurs that the bone has grown over the screw and healed to conform thereto. Counterclockwise rotation of the screw (as viewed from the surgeon) will tend to withdraw the screw from the bone, following the threaded path formed by the thread. The cutting faces 46 engage the bone material of the near cortex to permit continued withdrawal of the screws without use of extractor tools.

With prior screws, however, when the thread is withdrawn from the outer cortex at the far side of the bone, the proximal end of the thread crosses the medullary canal and contacts the outer cortex on the near side of the bone, where it encounters penetration resistance. The relatively hard outer cortex impedes retraction of the screw. More particularly, there is a risk that the thread of the bone screw will not engage the bone material, leaving the screw to turn freely and necessitating the use of an extractor tool. Screws with prior cutting flutes were also not altogether effective because the geometry of the flutes forming the reverse cutting threads did not adequately permit the thread to engage the bone. More particularly, the geometry of the thread pitch and flute size resulted in an insignificant axial offset of the cutting face from a leading thread forward of the flute (which leading edge has not entered the cortex). The amount of cutting face exposed to the cortex is inadequate to actually engage the cortex bone material. Consequently, it had been necessary to force prior screws into the outer cortex on the near side of the bone, thereby creating the risk that the screw would break.

With a fixation screw according to the present invention, however, the axial offset of the cutting faces 46 formed by flutes 44 is adequate to engage the bone. More particularly, with three flutes according to a less preferred form of the present invention, cutting faces 46 can be axially offset from the leading thread by as much as one-quarter of the thread pitch (which can be as much as one-half of the thread width, depending on root width). In the preferred form of the invention, only one reverse flute 44 forms a single set of reverse cutting faces so that the flute 44 is long enough (e.g., one-half the circumference of the screw or more) to ensure that the cutting face is axially offset from the leading thread by an amount up to the full width of the thread. Hence, the cutting faces react against the outer cortex at the surface adjacent the medullary canal, thereby cutting a path for thread 30 to withdraw through the outer cortex on the near side of the bone to fully withdraw the fixation screw therefrom. Alternatively or additionally, the tapered threads provide self-tapping of the bone at the near side for ease of withdrawal of the screw.

The flutes of the present invention are advantageous over the prior flutes by providing greater clearance for the cutting faces on the thread to first engage the bone matter without interference from thread on lands between the flutes. Moreover, the flute according to the present invention ensure that first contact to the bone tissue will be at the cutting face formed by the flute. Thus, as the screw is withdrawn through the medullary canal and the threads first contact the outer cortex at the near side of the bone, the cutting faces engage the outer cortex of the bone to ensure proper cutting of the bone to enable withdrawal of the screw. Additionally, bone chips and debris formed during the reverse cutting process is collected in the flutes for removal with the screw.

Although the present invention has been described with reference to preferred embodiments, workers skilled in the art will recognize that changes may be made in form and detail without departing from the spirit and scope of the invention.

What is claimed is:

1. A fixation screw for attaching to a bone, the screw having an axis about which the screw maybe rotated in a forward rotational direction to attach the screw to the bone and about which the screw may be rotated in a reverse rotational direction to remove the screw from the bone, the screw comprising:

an elongate shaft having a proximal end and a distal end;

a plurality of convolutions of thread on the shaft extending from the distal end toward the proximal end; and at least one flute transversing a proximal portion of the thread, the flute forming cutting faces on the thread, the cutting faces being formed in a first plane containing the axis of the screw, the flute further forming a base surface having a rotational portion coincident to a root diameter of the thread and a planar portion is a second plane tangential to the rotational portion, the first and second planes forming an angle greater than 90°, the cutting faces being arranged to cut the bone when the screw is rotated in the reverse rotational direction.

2. A screw according to claim 1 wherein a projection of the second plane intersects a projection of the first plane along a line parallel to the axis of the screw at least as distant from the axis of the screw as the crest diameter.

3. A screw according to claim 1 wherein the base surface of the flute is adjacent the cutting face such that when the screw is rotated in the reverse rotational direction the base surface will be forwardly of the cutting face.

4. A screw according to claim 1 wherein the thread has a pitch that is so disposed and arranged with the base surface of the flute that when the screw is rotated in the reverse direction a substantial portion of the cutting face is axially offset from the thread forwardly of the cutting face.

5. A screw according to claim 4 wherein the cutting face is offset from the thread forwardly of the cutting face by at least about one-quarter of the pitch of the cutting thread.

6. A screw according to claim 4 wherein the cutting face is offset from the thread forwardly of the cutting face by a substantial amount of the width of the thread.

7. A screw according to claim 1 wherein the thread of a group of convolutions adjacent the distal end of the shaft is tapered to form forward self-tapping threads.

8. A screw according to claim 1 wherein at least one distal flute at the distal end of the shaft, the flute forming second cutting faces on the thread to cut the bone when the screw is rotated in the forward rotational direction.

9. A screw according to claim 1 wherein drilling means is positioned at the distal end of the shaft.

10. A screw according to claim 1 wherein the plurality of convolutions of thread includes a distal group of convolutions having a root diameter larger than the diameter of the shaft and a crest diameter, and an adjacent proximal group of convolutions having a root diameter tapered between the root diameter of the thread of the distal group of convolutions and the diameter of the shaft and a crest diameter which is tapered from the crest diameter of the distal group of convolutions to the diameter of the shaft, the taper forming a reverse self-tapping thread.

11. A screw according to claim 10 wherein the crest of the tapered thread is sharp.

12. A fixation screw for attaching to a bone, the screw having an axis about which the screw maybe rotated in a forward rotational direction to attach the screw to the bone and about which the screw maybe rotated in a reverse rotational direction to remove the screw from the bone, the screw comprising:

an elongate shaft having a proximal end and a distal end;

a plurality of convolutions of thread on the shaft extending from the distal end toward the proximal end; and at least one flute transversing a proximal portion of the thread, the flute forming cutting faces on the thread, the cutting faces being formed in a first plane containing the axis of the screw, the flute further forming a base surface having a rotational portion coincident to a root diameter of the thread and a planar portion in a second plane tangential to the rotational portion, a projection of the second plane intersecting a projection of the first plane along a line parallel to the axis of the screw at least as distant from the axis of the screw as the crest diameter, the cutting faces being arranged to cut the bone when the screw is rotated in the reverse rotational direction.

13. A screw according to claim 12 wherein the base surface of the flute is adjacent the cutting face such that when the screw is rotated in the reverse rotational direction the base surface will be forwardly of the cutting face.

14. A screw according to claim 12 wherein the thread has a pitch that is so disposed and arranged with the base surface of the flute that when the screw is rotated in the reverse direction a substantial portion of the cutting face is axially offset from the thread forwardly of the cutting face.

15. A screw according to claim 14 wherein the cutting face is offset from the thread forwardly of the cutting face by at least about one-quarter of the pitch of the cutting thread.

16. A screw according to claim 14 wherein the cutting face is offset from the thread forwardly of the cutting face by a substantial amount of the width of the thread.

17. A screw according to claim 12 wherein the thread of a group of convolutions adjacent the distal end of the shaft is tapered to form forward self-tapping threads.

18. A screw according to claim 12 wherein at least one distal flute at the distal end of the shaft, the flute forming second cutting faces on the thread to cut the bone when the screw is rotated in the forward rotational direction.

19. A screw according to claim 12 wherein drilling means is positioned at the distal end of the shaft.

20. A screw according to claim 12 wherein the plurality of convolutions of thread includes a distal group of convolutions having a root diameter larger than the diameter of the shaft and a crest diameter, and an adjacent proximal group of convolutions having a root diameter tapered between the root diameter of the thread of the distal group of convolutions and the diameter of the shaft and a crest diameter which is tapered from the crest diameter of the distal group of convolutions to the diameter of the shaft, the taper forming a reverse self-tapping thread.

21. A screw according to claim 20 wherein the crest of the tapered thread is sharp.

* * * * *